(12) United States Patent
Hurwitz et al.

(10) Patent No.: US 7,682,575 B2
(45) Date of Patent: Mar. 23, 2010

(54) LOW COST, EASY TO MANUFACTURE SCENT DISPERSING MAT APPARATUS

(76) Inventors: Marni Markell Hurwitz, 81 Mosle Rd., Far Hills, NJ (US) 07931; Dave Narasimhan, 6 Summit Trail, Flemington, NJ (US) 08822

( * ) Notice: Subject to any disclaimer, the term of this patent is extended or adjusted under 35 U.S.C. 154(b) by 138 days.

(21) Appl. No.: 11/265,658

(22) Filed: Nov. 2, 2005

(65) Prior Publication Data

US 2006/0062700 A1    Mar. 23, 2006

Related U.S. Application Data

(63) Continuation-in-part of application No. 11/007,725, filed on Dec. 8, 2004, now Pat. No. 7,498,072, which is a continuation-in-part of application No. 10/712,343, filed on Nov. 14, 2003, now Pat. No. 6,991,842.

(51) Int. Cl.
    *A61L 9/00*    (2006.01)
(52) U.S. Cl. .................. 422/123; 422/120; 422/124; 428/71; 36/43; 36/44; 239/53
(58) Field of Classification Search .............. 422/123, 422/124, 120; 239/53; 401/265, 266; 36/43, 36/44; 15/215; 428/71
    See application file for complete search history.

(56) References Cited

U.S. PATENT DOCUMENTS

| 3,993,444 | A | | 11/1976 | Brown | 21/126 |
| 4,161,284 | A | | 7/1979 | Rattan | 239/43 |
| 4,254,179 | A | * | 3/1981 | Carson et al. | 428/316.6 |
| 4,346,059 | A | | 8/1982 | Spector | 422/125 |
| 4,695,434 | A | | 9/1987 | Spector | 422/116 |
| 4,876,135 | A | | 10/1989 | McIntosh | 428/74 |
| 5,261,169 | A | * | 11/1993 | Williford | 36/43 |
| 5,565,148 | A | | 10/1996 | Pendergrass, Jr. | 261/30 |
| 5,651,942 | A | | 7/1997 | Christensen | 422/125 |
| 5,744,209 | A | | 4/1998 | Parkes | 428/96 |
| 6,031,967 | A | | 2/2000 | Flashinski et al. | 392/390 |
| 6,154,607 | A | | 11/2000 | Flashinski et al. | 392/390 |
| 6,173,675 | B1 | | 1/2001 | Licciardo | 119/28.5 |
| 6,254,836 | B1 | | 7/2001 | Fry | 422/124 |
| 6,309,986 | B1 | | 10/2001 | Flashinski et al. | 442/125 |
| 6,315,482 | B1 | * | 11/2001 | Girardot et al. | 401/266 |
| 6,361,752 | B1 | | 3/2002 | Demarest | 422/306 |
| 6,425,530 | B1 | * | 7/2002 | Coakley | 239/52 |

(Continued)

*Primary Examiner*—Sean E Conley
(74) *Attorney, Agent, or Firm*—Ernest D. Buff & Associactes, LLC; Ernest D. Buff; Harry Anagnostopoulos

(57) ABSTRACT

A low cost, easy to manufacture scent-dispersing mat apparatus has a flexible closed cell foam mat containing a plurality of blind holes extending from its upper surface. These blind holes are partially filled with a fragrant liquid scent, creating air spaces thereabove. The upper surface of the flexible closed cell foam mat is sealed with a polymeric sheet that entraps the air spaces in the blind holes, causing entrapped air to become saturated with fragrant scent vapor. The polymeric sheet is perforated by one or more fine needles at the blind hole locations. The perforations permit escape of fragrant scent-saturated air to the ambient when pressure is applied to the top surface of the mat. Upon release of pressure, the foam mat and the blind holes recover their shape; the entrapped air pressure decreases, drawing fresh ambient air into the entrapped air spaces.

14 Claims, 1 Drawing Sheet

U.S. PATENT DOCUMENTS 6,551,560 B1 4/2003 Flashinski et al. ........... 422/125
6,581,915 B2 6/2003 Bartsch et al. ................ 261/26
6,722,578 B2 4/2004 Skalitzky et al. .............. 239/57

* cited by examiner

LOW COST, EASY TO MANUFACTURE SCENT DISPERSING MAT APPARATUS

This is a continuation-in-part of application Ser. No. 11/007,725, filed Dec. 8, 2004 now U.S. Pat. No. 7,498,072 entitled "Long-Service Life Scent Dispensing Mat Apparatus" which, in turn, is a continuation-in-part of application Ser. No. 10/712,343, filed Nov. 14, 2003 now U.S. Pat. No. 6,991,842, the disclosures of which are hereby incorporated in their entirety by reference thereto.

BACKGROUND OF THE INVENTION

1. Field of the Invention

The present invention relates to a low cost easy to manufacture mat apparatus for dispersing scent; and more particularly to an apparatus capable of housing a scented vaporizable liquid for dispersion of volatilized scent when the apparatus receives a force or is compressed.

2. Description of the Prior Art

Many patents address issues related to the dispersion of scent into a room, and in particular to the dispersion of scent by way of a scent dispersing apparatus in the form of a mat. The volatile fragrant oils in most of these patents require a heating element to evaporate the fragrance. In many cases, a blower is needed to disperse the scent into the room.

U.S. Pat. No. 3,993,444 to Brown discloses an intermittent time controlled vapor-dispensing device. This device has an open top container holding a quantity of a volatile paste-like material within the interior of the container, which material is intermittently dispensed in vapor form to the ambient atmosphere. An electric circuit controlled motor is intermittently energized at predetermined time intervals to rotate a fan in the device for specific time periods to direct currents of air onto the exposed surface of the paste. This transforms the paste into vapor that is discharged outwardly from the container. A portion of the device is defined by apertured walls that surround the container, with the apertures of sufficiently small size so that the container in the device is substantially concealed. The apertures serve several functions, including permitting air to flow into the interior of the device through a first portion, and discharging vapors through a second portion of the apertures. As the fan operates, the vapor from the paste material configures into a number of small streams and discharges outwardly through the second portion of the apertures, and disperses into the ambient atmosphere. In order to vaporize and disperse the paste, an electrical current is passed through a heater and the fan must be driven. The vapor-dispensing device disclosed by the patent is not a mat. Furthermore, the dispensing device requires electrical connection for heating and driving a fan in order to facilitate the vaporization, streaming and dispersion of the scent particuli.

U.S. Pat. No. 4,161,284 to Rattan discloses a deodorant or fragrance dispensing packet for use in vehicles and the like and is characterized by being quickly rechargeable by squeezing the two parallel sides of the packet together, which causes spikes molded on the interior of one side of the packet container to rupture a liquid fragrance containing pod, permitting the perfume to flow into a surrounding absorbent pad. The fragrance from the absorbent pad slowly evaporates and disseminates into the atmosphere through holes in the outer casing, which were punched by the consumer after purchase to permit the dissemination of the first charge of fragrance which was contained in the absorbent pad. This device expels liquid fragrance contained in a pad, not a fragrance containing air. The device is an air freshener, and the '284 patent does not disclose or suggest a scent dispensing mat.

U.S. Pat. No. 4,346,059 to Spector discloses an aroma-generating lamp structure in which a pad of porous material impregnated with an aroma-producing liquid is disposed under a vent in a substantially enclosed housing. An electrical heating element placed in the housing acts to heat and expand the air confined therein to create a positive air pressure, producing a pressure differential between the heated air and the atmosphere above the vent. Heated air is driven through the pad to rapidly volatilize the liquid and exude an aromatic vapor through the vent into the atmosphere. This aroma-generating lamp is not a mat and relies on lamp heat to drive the aroma into the atmosphere.

U.S. Pat. No. 4,695,434 to Spector discloses an aroma-generating unit. The aroma-generating unit is adapted to periodically discharge bursts of aromatic vapor into the atmosphere, with non-aromatic intervals between the bursts. These non-aromatic intervals have duration sufficient to avoid desensitizing the olfactory response of those exposed to the unit. The unit includes a hollow case whose upper wall has a vent therein and whose sidewall has a slot to receive a replaceable cartridge provided with a porous mat impregnated with an aromatic liquid. When fully inserted, the cartridge is disposed below the vent and defines an air-confined chamber within the case. Disposed in this chamber is an electrical heater that is periodically energized by power pulses to heat and expand the confined air and to produce a positive pressure in the chamber forcing the heated air through the impregnated mat to rapidly volatilize the liquid. Bursts of aroma are produced and discharged into the atmosphere through the vent, and are separated by relatively long, non-aromatic intervals. The disclosed aroma-generating unit is not a mat, and utilizes electrical heat to produce a positive pressure of the aroma vapor.

U.S. Pat. No. 4,876,135 to McIntosh discloses a floor mat with disposable absorbent pad. The automobile floor mat comprises a jacket member having a throat opening in a free edge for receiving an insert sheet of absorbent material, such as cardboard. The top sheet of the jacket has openings for the passage of foreign matter, including spilled liquids. The insert sheet is disposed under the top sheet and retains foreign matter disposed thereon through the openings in the top sheet. The back surface of the insert is coated with a water resistant coating. After the insert sheet is soiled it can be removed and cleaned or replaced by a new sheet with the soiled sheet discarded. The insert sheet may be coated with a deodorizing liquid that releases a pleasant smelling scent especially when the floor mat is used in an automobile. The insert sheet is supposed to absorb liquids. To meet this functionality, the cells in the sheet must be empty and therefore they cannot contain any significant reservoir of vaporizable scent. Furthermore, the automobile mat provided by the patent is not cushioned since the insert sheet is rigid.

U.S. Pat. No. 5,565,148 to Pendergrass, Jr. discloses a device for selectively providing a multiplicity of aromas. The device may deliver one or more aromas at selected times and include a housing with a receptacle and an aroma delivery device detachably received in the receptacle. A reservoir contains a volatile aroma material and a diffusion rate-controlling structure which at least partially covers the reservoir to provide controlled release of the aroma. The aroma delivery device includes a carrier having a plurality of aroma-bearing elements that are selectively communicated with an air passageway for providing one or more aromas as desired. The device is especially useful for providing a realistic sensory experience in an interactive or non-interactive use, and may be used in such diverse settings as the entertainment industry, the educational training field or a medical arena. This multiplicity aroma device is not a mat. It requires the opening of diffusion controlling structure to release selected aroma.

U.S. Pat. No. 5,651,942 to Christensen discloses an aromatic fragrance generator. The aromatic fragrances generator is provided for supplying aromatic fragrances to the atmosphere. The fragrance generator employs a heating element in a container to heat a fragrance base material contained in a receptacle to supply a pleasant aroma to the atmosphere, primarily to eliminate bathroom and kitchen odors. The disclosed fragrance generator does not involve a mat capable of releasing scent upon subjection to force. Rather, the disclosed generator utilizes a heating element and a fragrance base material that must be heated in order to release fragrance into the atmosphere.

U.S. Pat. No. 5,744,209 to Parkes discloses a scented mat product and method for making the mat product. The patent discloses a low cost, high quality, durable mat product having a fragrance or scent incorporated in the backing material thereof. The backing has a polyvinyl chloride based composition so that the scent is evenly dispersed throughout the environment of the mat for an extended period of time. Also disclosed is a method for making the mat product by adding a scent or fragrance to the backing material used in the mat product prior to securing the backing material to a textile layer. The disclosed mat provides for the scent to be retained in the backing layer, from which the scent is always evaporating. As a result of constant evaporation, the mat inherently has a limited usable lifetime. The scent soon becomes virtually exhausted, causing the mat to have a short duration as a scented product.

U.S. Pat. No. 6,173,675 to Licciardo discloses aromatherapy mats for pets. The mattress, mat or bed for animals comprises a soft and comfortable mat which-contains aromatherapy herbs having volatile components which aid and enhance certain behaviors in cats and dogs when laid upon. The mat is constructed with layers of soft fiber filling material, and herbs are arranged between the layers and an outer cover of the mat. The scent and volatile effects of the herbs emerge through the layers of the filling material and are inhaled by the pet to render the desired behavior. The mat relies on volatile components from the herb, which evaporate through the porous soft fiber layer; but the quantity of volatile aroma in herbs is inherently small. Moreover, the constant evaporation required for operation of the mat produces a very limited time for aroma release.

U.S. Pat. Nos. 6,031,967, 6,154,607 and 6,309,986 to Flashinski, et al. disclose mats that dispense volatile materials. The multi-layered mats are especially suited to dispense volatile vapors such as insecticides. One layer forms a carrier layer impregnated with the volatile. It is secured to at least one metal layer. The metal layer spreads the heat from a heater, thereby minimizing hot spots. Additional layers may be provided to facilitate a further heat distribution or temperature step down. An air gap can be provided between two of the layers. The disclosed mat is a heated device requiring heating in order to release volatile vapors. The volatile vapors are not released merely by the exertion of force upon the mat.

U.S. Pat. No. 6,254,836 to Fry discloses a device for an air freshener for use by hanging in an automobile or other location made in a variety of Native American shapes. The device is provided with a circular bulb on its backside and the device further contains an amount of absorbent material held in a recessed space in its body for holding liquid scented oil. The scent can be dispersed into the atmosphere by selectively depressing and releasing the bulb so that an amount of air is dispelled through scent apertures into the air space surrounding the air freshener. In an alternative embodiment, the bulb is threaded into the air freshener and contains an amount of absorbent material whereby scent oil is placed directly on the absorbent material therein, which then can be displaced into the air surrounding the air freshener by pressing on the bulb with the scent passing through the air apertures. The operation of this device requires squeezing a bulb, which expels an air-containing fragrance. The device is an air freshener for an automobile, not a scent-dispersing mat.

U.S. Pat. No. 6,361,752 to Demarest, et al. discloses an apparatus for volatilizing and dispensing a chemical into a room environment. An air quality modification apparatus dispenses a volatile material, such as for scenting the air, controlling pests, allergen control, or the like. The apparatus includes an electric motor having a rotor and a coil. When electric current is applied, the coil produces both heat and an electromagnetic field that causes rotation of the rotor. A source of the volatile material is located adjacent to the coil so as to be volatilized by the coil's heat. An impeller, attached to the rotor, moves air across the volatile material and blows the vapors away from the apparatus. Energy efficiency is provided by employing the electric motor coil as the source of heat to vaporize the volatile material. Also disclosed is a refill supply of a volatile material for use with such an air quality modification apparatus. This apparatus is not a mat. It must be heated by an electrical current and a fan to drive the vapors into the atmosphere.

U.S. Pat. No. 6,551,560 to Flashinski, et al. discloses a two-stage dispensing mat. The two-stage mat is comprised of two materials varying either in thickness, thermal conductivity and/or porosity (and coated with like volatile material), or coated with volatile materials having different vaporization pressures. When the mat is heated, the two mats volatilize the fragrance at different rates. This creates an instant burst of volatile, followed by a sustained vaporization of volatile. Methods of using such mats are also disclosed. The disclosed mat must be heated to evaporate a volatile fragrance from a two-stage mat; the fragrance is evaporated from the mat at different rates.

U.S. Pat. No. 6,581,915 to Bartsch, et al. discloses a dispensing device for dispensing scents. The dispensing device dispenses scents into the environment and contains one or more scents or aromatic materials. The dispensing device includes a housing and a removable, reusable/replayable, closed, multiple scent-containing article, which is removably inserted into or onto the housing. The scent is released by unlocking a scent closure mechanism. Once the scent closure mechanism is unlocked, the fragrance constantly evaporates. The disclosed dispensing device is not a mat. No provision is made for controlled release of scent through application of force upon a surface. Rather, the device continuously dissipates scent upon release of a closure mechanism.

U.S. Pat. No. 6,722,578 to Skalitzky, et al. discloses an apparatus for dispensing volatile materials. A dispenser with a lid laminate providing controlled release of a volatile material contained in a tray is disclosed. The lid includes a vapor impermeable, removable outer laminate and a vapor permeable inner layer covering an open side of the tray. The outer laminate includes layers of polyethylene terephthalate (PET) and aluminum foil removably adhered to the inner layer of biaxially oriented polypropylene (OPP) by an ethylene acrylic acid copolymer. Bottom and sidewalls of the tray are constructed of a metal/polymer pressure-formed colored tray laminate impermeable to the vapors and volatile material. The tray has a peripheral lip with an outer surface of cast polypropylene to which the vapor permeable inner layer of the lid is heat-sealed. Fragrant vapor is released continuously once the barrier is removed. The apparatus disclosed by the '578 patent is not a mat.

There remains a need in the art for a cushioned mat, which reliably dispenses scent when stepped or pressed upon without continuously releasing the fragrance, thereby providing an extended service life for mats used on household floors, pet beds and land vehicles.

SUMMARY OF THE INVENTION

The present invention provides a low cost easy to manufacture scent-dispersing mat apparatus, comprising a flexible close cell foam mat member composed of a rubber or polymeric material. The polymeric material for the close cell foam mat member is selected from the group consisting of neoprene, chloroprene, silicone or other suitable elastomeric material. The flexible close cell foam mat member has an upper surface, lower surface and side surfaces. Since the flexible close cell foam mat member comprises closed cells which contain air, and the cells intimately contact each other, the foam mat can be compressed easily with a springy feel, and the air contained within each closed cell does not escape. This is in sharp contrast with an open cell foam, wherein the cells are open to the ambient and air leaks out when the foam is compressed. Due to the interlocking nature of cells in the closed cell foam mat, any liquid applied to the foam or contained within the foam mat does not leak. The invention takes advantage of this property of the closed cell foam mat to contain a liquid scent, which is voltalizable at the ambient temperature. This close cell foam mat typically has length dimension ranging from about 2 to 10 feet long, and preferably about 3 to 6 feet long. The width dimension is typically about 1 foot to 5 feet, and preferably 2 feet to 4 feet. The thickness of the closed cell foam mat ranges from about 0.25 inches to 2 inches.

The upper surface of the closed cell foam mat is provided with a multitude of drilled holes or molded holes that are produced when the close cell foam mat is produced. These holes or apertures have a an average effective diameter in the range of 0.1 inches to 0.5 inches. They do not reach the bottom surface of the flexible foam mat and are in essence 'blind' holes. These apertures or holes may be of any shape, including circular, square shaped, rectangular shaped or arbitrary (random) shape. These blind holes may be spaced in any desired manner and are typically located at a spaced relationship selected by the manufacturer. Generally, it is desirable that the spacing between the blind holes be at least 3 times the diameter of the blind hole so that the compression properties of the flexible close cell foam mat is not compromised.

During the manufacture of the low cost easy to manufacture scent-dispensing mat, these blind holes are partially filled with a volatalizable scent liquid to a level less than 50%. At this stage, an air space is present above the scent liquid. The filled scent liquid does not seep through the closed cell foam, and is entirely contained within the blind holes. A sheet of polymeric material with a thickness in the range of about 0.002 inches to 0.0030 inches is now bonded to the upper surface of the flexible closed cell foam mat to seal the liquid scent containing blind holes. This bond between the polymeric sheet and the flexible closed cell foam may be accomplished by a number of methods including adhesive bonding, thermal bonding and the like. At this stage all the blind holes containing liquid scent are completely sealed. Now, one or more fine needles are used to perforate the polymeric sheet at the blind hole locations. Passage of one or more needles through the polymeric sheet creates one or more perforated holes in the polymeric sheet at the blind hole locations, but they immediately close off as the needles are withdrawn. The liquid scent contained in the blind holes does not readily leak through these needle created perforations. Typical needle diameter is 0.001 to 0.030 inches resulting in perforations in the range of 0.001 to 0.030 inches.

The low coat easy to manufacture scent dispensing mat apparatus is used with the polymeric sheet facing the user. When the user steps on the mat, the flexible closed cell foam mat compresses readily and the air pressure within the blind holes above the liquid scent increases rapidly due to the deformation of the mat. This increased pressure allows the air contained within the blind holes to escape through the perforations in the polymeric sheet. The escaping air contains the voltalized liquid scent at a concentration approaching the equilibrium saturation value. As a consequence, the mat disperses the fragrance effectively when the user steps or presses on its upper surface. When pressure on the mat is released, the flexible closed cell foam mat returns to its original shape, creating a vacuum within the blind holes. Ambient air is drawn into the air space of the blind holes through the perforations. The liquid scent contained in the blind holes evaporates slowly, enriching the air in the blind hole to an equilibrium saturation value. Upon achieving equilibrium saturation, the air is again ready to be released by pressure applied to the upper surface of the mat.

BRIEF DESCRIPTION OF THE DRAWING

The invention will be more fully understood and further advantages will become apparent when reference is had to the following detailed description of the preferred embodiments of the invention and the accompanying drawing, in which.

DETAILED DESCRIPTION OF THE INVENTION

Figure 1:
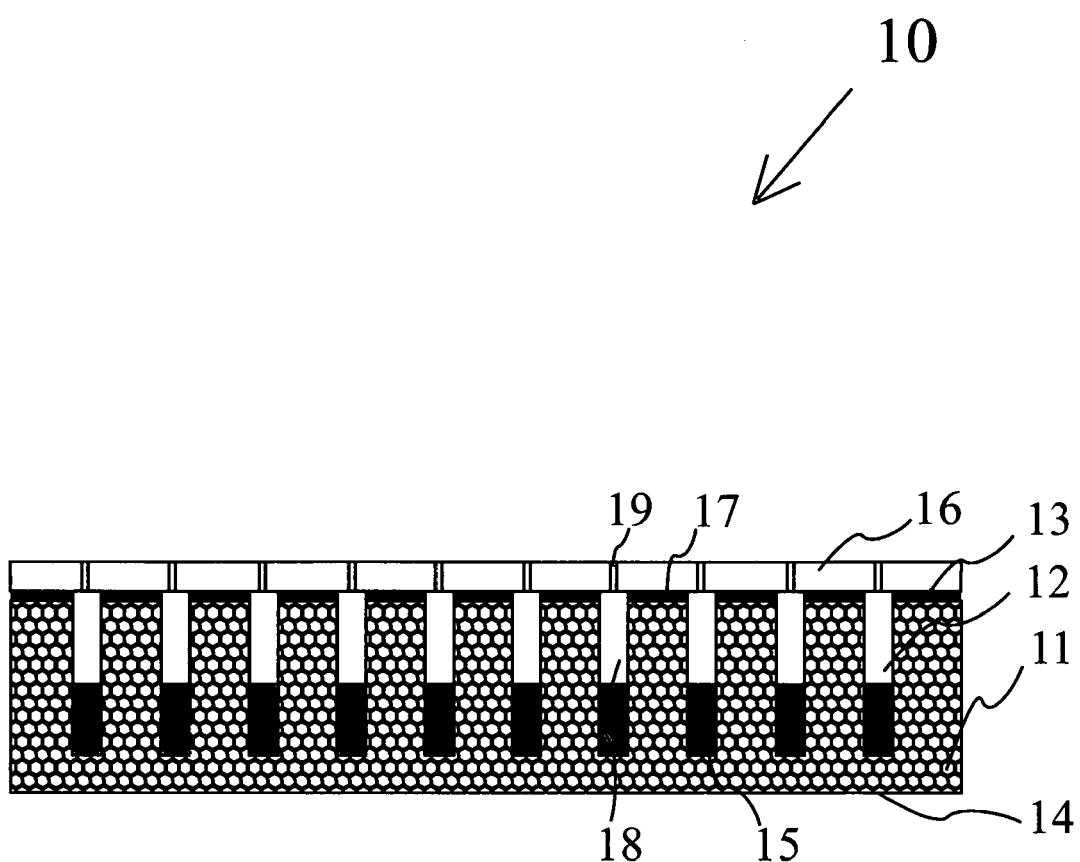
FIG. 1 is a diagrammatic representation of a low cost easy to manufacture scent-dispersing mat that incorporates the elements of the present invention.

The scent dispersing mat apparatus of the present invention releases a scented fragrance when force is applied to its external upper surface. Such force is exerted when, for example, the upper surface of the mat is stepped on by a person, animal or inanimate object. The scent dispersing mat apparatus also provides a cushioned contact that affords a comfortable surface for stepping, sitting or lying upon.

Generally stated the scent dispersing mat is easy to use and disperses fragrant scent only when the force is applied to the upper surface of the mat, for example by a user stepping on the mat. The mat comprises a flexible closed cell foam mat with multitude of molded or drilled holes or apertures which are open to the upper surface but do not reach the bottom surface of the mat and therefore forming 'blind' holes or apertures. A plurality of these holes is partially filled with a liquid scent leaving an air space above the liquid scent, which vaporizes at ambient temperature. Therefore, an air space exists between the liquid scent and the upper surface of the flexible close cell mat. A polymeric sheet is then bonded to the upper surface of the flexible closed cell mat to seal each of the blind holes containing liquid scent and entrapped air. The polymeric sheet is perforated with one or more fine needles at the blind hole locations. These fine perorations are small enough to prevent the escape of the liquid scent. Moreover, due to the elastic nature of the polymeric sheet, these fine perforations instantly close as the needles are withdrawn.

The liquid scent present in a plurality of the blind holes evaporates the scent into the entrapped air, saturating the air with the liquid scent vapor. The air is rapidly brought to the equilibrium saturation vapor pressure of the liquid scent at the ambient temperature. This equilibrium value represents the maximum value of scent vapor that air can carry at the ambient temperature.

During use, the mat is placed with the polymeric sheet as the upper surface of the scent-dispensing mat. When pressure is applied to the scent-dispensing mat by stepping or otherwise pressing on the mat, the flexible closed cell foam mat compresses readily. This compression results in increased air pressure within the blind holes that contain liquid scent and entrapped air saturated with liquid scent vapor. Due to the closed cell construction of the flexible closed cell foam, the liquid scent is incapable of escaping from the blind holes in spite of the applied compression. However, the increased entrapped pressure in the blind holes can easily open the needle-punctured perforations in the polymeric sheet bonded to the upper surface of the flexible closed cell foam mat. This dispenses the saturated scent vapor to the ambient perfuming the air space around the mat as the user steps on the mat.

When the pressure is released, the flexible close cell foam mat immediately returns to its original shape. This brings the compressed blind holes to their original shape, creating a reduced pressure or near vacuum in the entrapped air space above the liquid scent in the blind holes. The perforations now open in an opposite direction to that during scent release, drawing ambient air into the blind holes. The liquid scent vapor pressure in the entrapped air within the blind hole is well below the equilibrium saturation value due to ingress of ambient air during blind hole recovery. Gradually, the liquid scent evaporates to saturate the vapor in the entrapped air to equilibrium saturation value. When the entrapped air attains equilibrium saturation, the scent-dispersing mat is ready to be stepped on by the user.

The manufacturing procedure for the scent-dispensing mat is inherently a low cost process. A closed cell mat made from neoprene, chloroprene, silicone or other suitable elastomeric material is provided with a multitude of blind holes. These blind holes may be formed during the manufacture of the closed cell foam mat or created by drilling or other suitable machining means. Scent liquid is applied until the blind holes of the flexible closed cell foam mat are partially filled. The blind holes of the mat are sealed by application of a polymeric sheet, which covers the open, blind holes at the upper surface of the flexible closed cell foam mat. Bonding of the polymeric sheet to the upper surface of the mat may be conveniently accomplished by use of an adhesive or thermal process well known in the art. Next, the polymeric sheet is perforated by passing one or more fine needles at the blind hole locations to create air flow passages. When the needle is withdrawn, these perforations inherently close due to the elasticity of the polymeric sheet preventing leakage of the liquid scent contained within each blind hole. However, when pressure is applied to the scent-dispensing mat, these perforations allow the discharge of scent-saturated, entrapped air to the ambient due to the increased pressure within the blind holes. The same perforations draw air from the ambient when pressure on the mat is released leading to the shape recovery of the blind holes.

Referring to FIG. 1, there is shown generally at 10 a low cost easy to manufacture scent-dispensing mat. A flexible close cell foam mat is shown at 11, which has a multitude of blind holes or apertures 12 therein. The flexible closed cell foam mat has an upper surface 13 and a bottom surface 14. A plurality of the blind holes are partially filled with a liquid scent 15. A polymeric sheet 16 is bonded to the upper surface 13 of the flexible closed cell foam mat using an adhesive 17. This creates an entrapped air space 18 above the liquid scent 15 within the blind hole 12. The polymeric sheet 16 is perforated with one or more fine needles to create perforations 19 at a plurality of the blind hole locations, through which liquid scent vapor containing entrapped air is dispensed into the ambient when the scent dispensing mat is compressed, and ambient air is drawn in when the compression is released.

The key features of the scent-dispersing mat include, in combination, the features set forth below:

1. a flexible closed cell foam mat with an upper surface and a bottom surface;
2. the upper surface of the mat is provided with a plurality of blind holes or apertures, the depth of which is less than the thickness of the flexible closed cell foam mat, so that the blind holes do not reach the bottom surface thereof;
3. a plurality of the blind holes are partially filled with liquid scent;
4. the upper surface of the flexible closed cell foam mat is sealed by a polymeric sheet by a sealing means that creates entrapped air spaces above liquid scent within the blind holes;
5. the sealing means comprises adhesive sealing and thermal sealing;
6. the polymeric sheet is provided with one or more perforations created by passing one or more fine needles through the polymeric sheet at blind hole locations;
7. the liquid scent within blind holes evaporates, forming liquid scent vapor within entrapped air spaces of the blind holes, creating equilibrium saturation of scent vapor in the entrapped air;
8. stepping or otherwise pressing on the scent dispensing mat compresses the flexible closed cell foam mat, thereby increasing air pressure within the entrapped air spaces within the blind holes, releasing liquid scent saturated air into the ambient through perforations in the upper surface of the mat;
9. releasing pressure on the scent-dispensing mat allows recovery of the flexible close cell foam to its original shape, thereby decreasing entrapped air pressure within the blind holes and drawing ambient air into the entrapped air spaces.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. A scent dispersing mat apparatus, comprising;
  a. a flexible closed cell foam mat having an upper surface and a bottom surface and a mat thickness;
  b. said upper surface having a plurality of blind holes or apertures therein, each of the blind holes having a depth smaller than the thickness of the said flexible closed cell foam mat, so that the depth of the blind holes is less than that required for contact with said bottom surface;
  c. a plurality of said blind holes being partially filled with liquid scent, to thereby provide a plurality of air spaces between said liquid scent and said upper surface;
  d. an impermeable polymeric material forming a sheet, said polymeric sheet covering and sealing said blind holes at said upper surface of said foam mat;
  e. attachment means, attaching said polymeric sheet to said upper surface of said flexible cell foam mat, thereby creating entrapped air spaces between said liquid scent and said polymeric sheet;
  f. said entrapped air becoming saturated with scent vapor by evaporation of said liquid scent;

g. said polymeric sheet being perforated by one or more fine needles to create perforations, said perforations being adapted to provide for communication between entrapped air within said blind holes and ambient air;

h. said perforations adapted to release scent saturated entrapped air when pressure is applied to the top surface of said mat, and said perforations adapted to draw ambient air into said blind holes when said pressure is released;

whereby said perforations are sufficiently small such that, due to the elastic nature of said polymeric sheet, said perforations will instantly close when no force is being applied to said mat; and whereby exertion of force on said mat squeezes said flexible closed cell foam mat, increasing pressure of said scent saturated entrapped air and opening said perforations, thereby releasing said scent saturated air into the ambient; and whereby upon release of said force said mat recovers its shape and the shape of blind holes, reducing said entrapped air pressure and drawing ambient air into said blind holes.

2. A scent dispersing mat apparatus as recited by claim 1, wherein said flexible closed cell foam is composed of neoprene, chloroprene, silicone or elastomeric material.

3. A scent dispersing mat apparatus as recited by claim 1, wherein said flexible closed cell foam has a length of about 2 feet to 10 feet.

4. A scent dispersing mat apparatus as recited by claim 3, wherein said flexible closed cell foam has a length of about 3 feet to 6 feet.

5. A scent dispersing mat apparatus as recited by claim 1, wherein said flexible closed cell foam mat has a width of about 1 foot to 5 feet.

6. A scent dispersing mat apparatus as recited by claim 5, wherein said flexible closed cell foam mat has a width of about 2 feet to 4 feet.

7. A scent dispersing mat apparatus as recited by claim 1, wherein said flexible closed cell foam mat has a thickness of about 0.25 to 2 inches.

8. A scent dispersing mat apparatus as recited by claim 1, wherein said plurality of blind holes have an average effective diameter in the range of about 0.1 to 0.5 inches.

9. A scent dispersing mat apparatus as recited by claim 8, wherein said plurality of blind holes are spaced apart by a distance at least 3 times said effective average diameter.

10. A scent dispersing mat apparatus as recited by claim 1, wherein said plurality of blind holes are less than 50% filled with said liquid scent.

11. A scent dispersing mat apparatus as recited by claim 1, wherein said polymeric sheet has a thickness in the range of about 0.002 inches to 0.0030 inches.

12. A scent dispersing mat apparatus as recited by claim 1, wherein said attachment means comprises an adhesive attachment means.

13. A scent dispersing mat apparatus as recited by claim 1, wherein said attachment means comprises a thermal attachment means.

14. A scent dispersing mat apparatus as recited by claim 1, wherein said perforations range in diameter from about 0.001 inches to 0.030 inches.

* * * * *